United States Patent [19]
Servidio

[11] Patent Number: 6,129,764
[45] Date of Patent: Oct. 10, 2000

[54] MODULAR PROSTHETIC JOINT COMPONENTS

[75] Inventor: Damon J. Servidio, Montville, N.J.

[73] Assignee: Stryker Technologies Corporation, Kalamazoo, Mich.

[21] Appl. No.: 09/199,148

[22] Filed: Nov. 24, 1998

[51] Int. Cl.[7] ..................................................... A61F 2/40
[52] U.S. Cl. ................................... 623/19.11; 623/23.11; 623/23.13
[58] Field of Search ................................ 623/18, 19, 22, 623/23

[56] References Cited

U.S. PATENT DOCUMENTS

| 5,222,984 | 6/1993 | Forte | 623/22 |
| 5,507,818 | 4/1996 | McLaughlin | 623/23 |
| 5,728,161 | 3/1998 | Camino et al. | 623/19 |

FOREIGN PATENT DOCUMENTS

| 2664809 | 1/1992 | France | 623/19 |

*Primary Examiner*—David J Isabella
*Attorney, Agent, or Firm*—Lerner, David, Littenberg, Krumholz & Mentlik, LLP

[57] ABSTRACT

Modular prosthetic shoulder components include a number of different sized humeral heads, each having a spherical outer surface and an interior tapered bore, a frustroconical intermediate head component dimensioned to lockingly mate with the tapered bore of the humeral heads and having a diametrical slot, and a humeral stem trunnion component having a rectilinear peg dimensioned to lockingly engage the diametrical slot in the intermediate head component. The components are assembled by inserting the intermediate head component into the tapered bore of a humeral head, inserting the peg of the trunnion component into the slot of the intermediate head component, and pressing the components together. The intermediate head component taper locks with the humeral head and force-fit locks onto the peg of the trunnion component. Prior to pressing the components together, the humeral head is movable relative to the trunnion component in three planes thereby allowing the practitioner to locate the humeral head in the same position as the organic humeral head which is being replaced. The components of the invention may also provide utility in other prosthetic joints such as prosthetic hip joints.

26 Claims, 5 Drawing Sheets

FIG. 10 under construction...

MODULAR PROSTHETIC JOINT COMPONENTS

BACKGROUND OF THE INVENTION

1. Field of the Invention

The invention relates to prostheses for replacement of a portion of a joint such as, for example, the upper portion of the humerus. More particularly, the invention relates to modular components for replacement of a portion of a joint.

2. State of the Art

For the sake of illustration only and without intending to limit the spirit or scope of the invention, the State of the Art and description of the invention that follows will be set forth in the context of a modular prosthesis for replacing a portion of the human shoulder.

Those skilled in the art will readily be able to apply the teachings set forth herein in the exemplary shoulder context, to provide modular components for the replacement of other joints, such as hip joints, etc., The human shoulder joint (glenohumeral joint) comprises two major components: the glenoid cavity (glenoid) which is part of the arm and the humeral head (humerus) which is part of the torso. Prosthetic shoulders also comprise glenoid and humeral components. The classical prosthetic humeral component is known as the NEER-type and is a one-piece component which is available in many different sizes for replacement of the upper portion of the organic humerus.

The classical humeral component has a stem which is designed to extend downwardly into a cavity formed within the organic humerus and which is secured with cement or with coatings which promote bone ingrowth to secure the stem. The stem is provided with a generally hemispherical head portion which is configured to replace the head of the organic humerus.

One of the disadvantages of the unitary NEER-type humeral components is the necessity of maintaining a large inventory of different sizes to accommodate different bone sizes in different patients. In addition to the necessity of providing different sized humeral components, it has been recognized that orientation of the humeral head relative to the stem also varies from patient to patient. For these reasons, various modular humeral components have been proposed.

On type of modular humeral component is described in U.S. Pat. No. 5,358,526 to Tornier. The Tornier prosthesis is shown in prior art FIG. 1.

Figure 1:
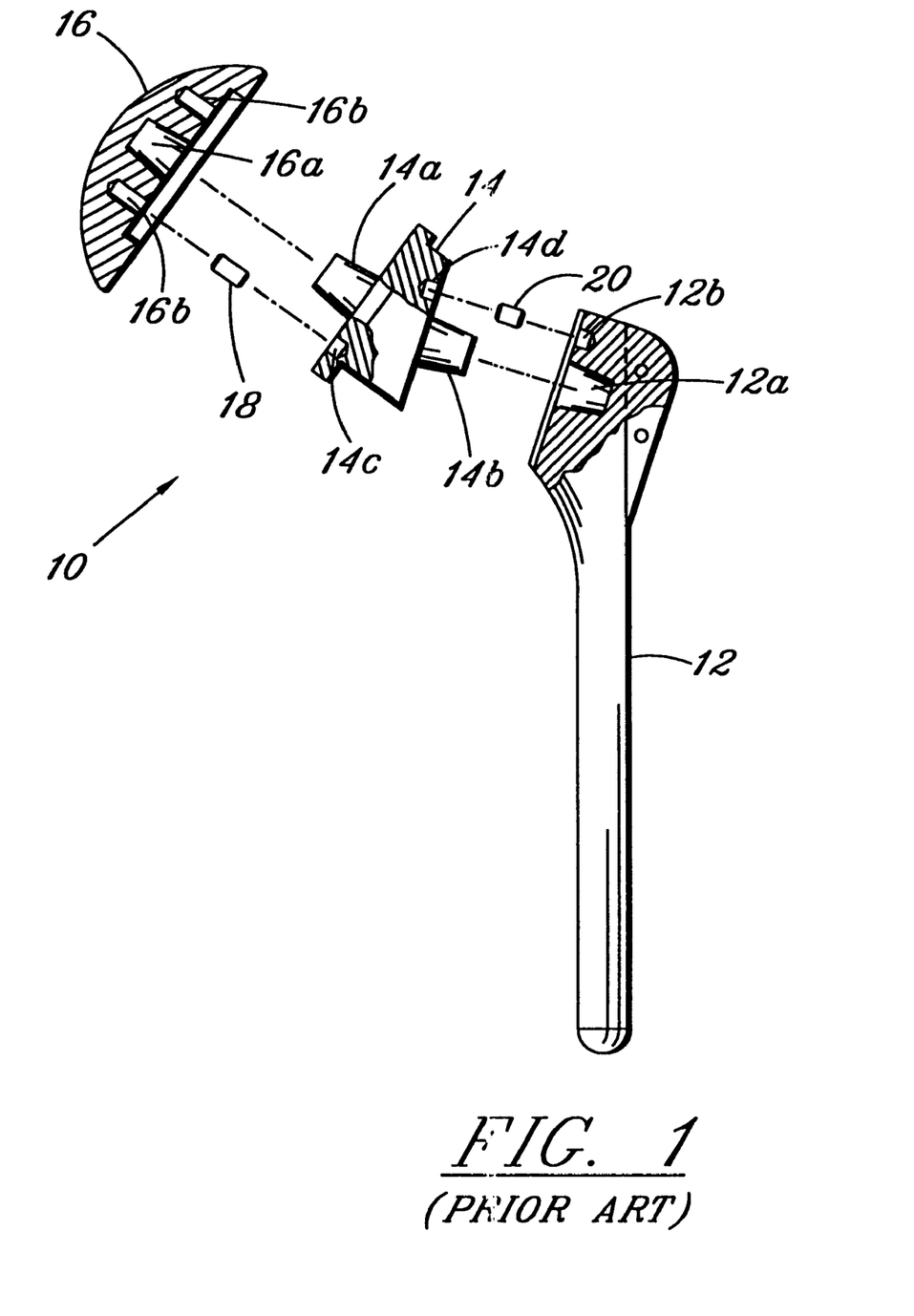
FIG. 1 is an exploded side elevational view in partial section of a modular prosthesis according to the prior art.

Referring to FIG. 1, the prosthesis 10 generally includes a stem portion 12, a spacer 14, and an hemispherical cap 16. The spacer 14 has opposite tapered studs 14a, 14b.

The stem 12 has a tapered bore 12a which is dimensioned to lockingly engage the stud 14b and the cap 16 has a tapered bore 16a which is dimensioned to lockingly engage the stud 14a. The bore 16a in the cap 16 is also offset from the geometrical center of the hemispherical cap 16 so that the angular orientation of the cap relative to the stud 14a is variable about the axis of the stud 14a.

A plurality of positioning bores 16b are provided in the cap 16, the bores 16b being arranged in a circle about the bore 16a. An index bore 14c is provided in the spacer 14 adjacent to the stud 14a. The angular orientation of the cap 16 relative to the spacer 14 is fixed with the aid of a pin 18 which engages the index bore 14c and one of the positioning bores 16b.

Blind holes 12b and 14d are provided in the stem 12 and spacer 14 respectively and a second pin 20 is provided to engage these blind holes to lock the angular position of the spacer relative to the stem. The stem and spacer are not, however, angularly adjustable.

Though not specifically taught by Tornier, it is presumed that the three components (stem, spacer, and cap) are provided in a variety of sizes and may be mixed and matched to assemble a humeral component which is best suited for a particular patient.

Another approach to modularity in a humeral component is disclosed in U.S. Pat. No. 5,314,479 to Rockwood, Jr. et al. and is illustrated in prior art FIG. 2.

Figure 2:
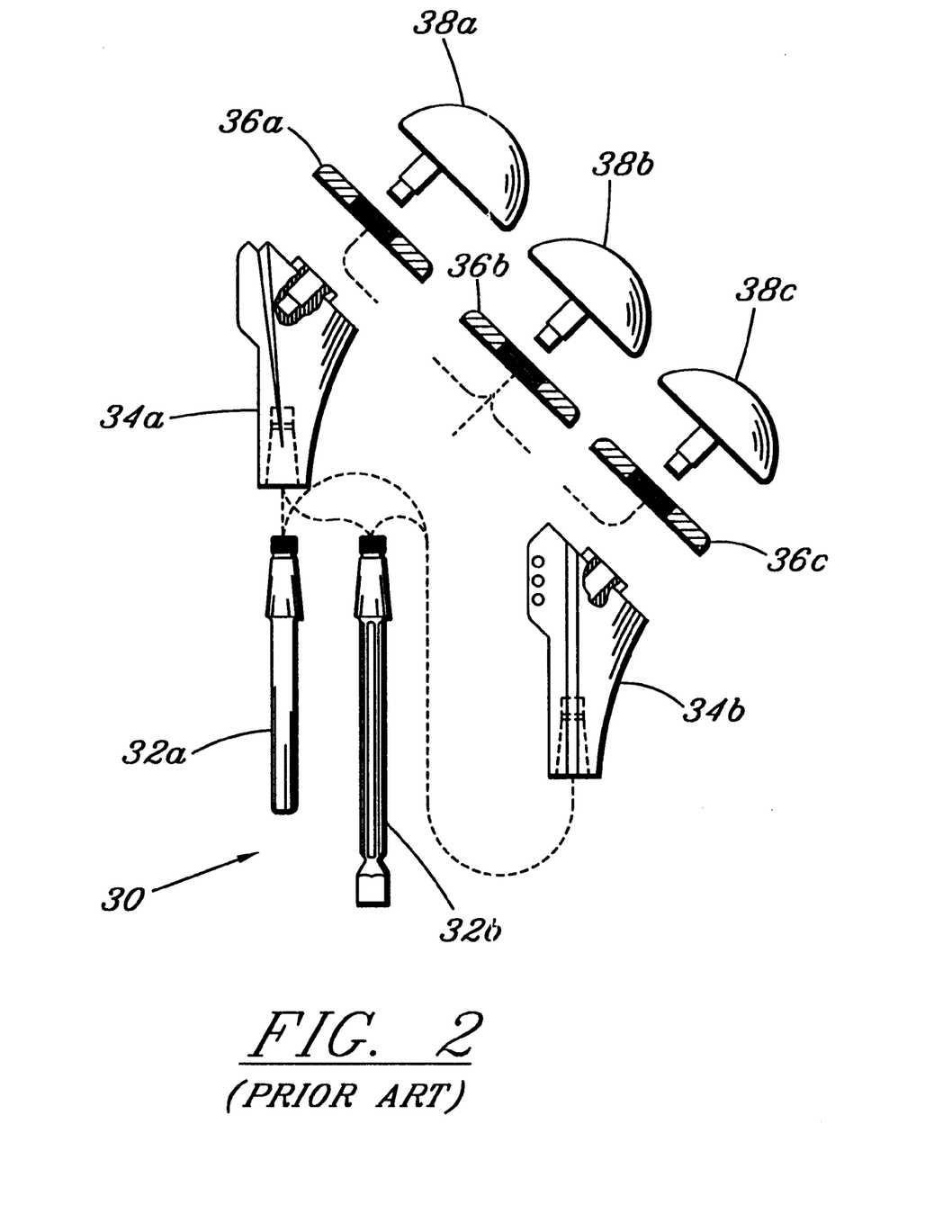
FIG. 2 is an exploded side elevational view in partial section of a modular prosthesis kit according to the prior art.

The '479 patent discloses a kit 30 which includes a plurality of different sized stems 32a, 32b, a plurality of different sized "bodies" 34a, 34b, a plurality of different sized collars 36a, 36b, 36c, and a plurality of different sized head members 38a, 38b, 38c. The components are mixed and matched to assemble a humeral component which is best suited for a particular patient.

The kit provided by the '479 patent provides a similar degree of customization as the modular component described by Tornier.

Recent anatomic studies of the humeral head indicate that the head angle, head center, and retroversion may vary significantly among patients.

While the modular components of the prior art are an improvement over the classical NEER-type prosthesis, the adaptability of these modular prostheses is limited, particularly in view of the recent anatomic studies of the humeral head.

Moreover, as may be appreciated from the prior art disclosures, the modular prostheses of the prior art are relatively complex and require elaborate assembly steps.

SUMMARY OF THE INVENTION

It is therefore an object of the invention to provide modular prosthetic shoulder components which enable the assembly of a humeral component which is best suited for a particular patient.

It is also an object of the invention to provide modular prosthetic shoulder components which enable variable orientation of the humeral head component relative to the humeral stem component.

It is another object of the invention to provide modular prosthetic shoulder components which enable variable angular orientation of the humeral head component relative to the humeral stem component in more than one plane.

It is still another object of the invention to provide modular prosthetic shoulder components which enable infinitely variable angular orientation of the humeral head component relative to the humeral stem component.

Yet another object of the invention is to provide modular prosthetic shoulder components which are easy to assemble.

Still another object of the invention is to provide modular prosthetic joint components in general (i.e., not limited to modular shoulder joint components) which realize the aforestated objects set forth relative to modular prosthetic shoulder components.

In accord with these objects which will be discussed in detail below, the modular components of the present invention (again, described for the sake of illustration only in the context of modular shoulder joint components) include a plurality of different sized humeral heads, each having a spherical outer surface and an interior tapered bore, a frustroconical intermediate head component dimensioned to lockingly mate with the tapered bore of the humeral heads and having a diametrical slot, and a humeral stem trunnion component having a rectilinear peg dimensioned to lockingly engage the diametrical slot in the intermediate head component.

The components are assembled by partially inserting the intermediate head component into the tapered bore of a humeral head, inserting the peg of the trunnion component into the slot of the intermediate head component, and pressing the components together.

The intermediate head component taper locks with the humeral head and force-fit locks onto the peg of the trunnion component. Prior to pressing the components together, the humeral head is movable relative to the trunnion component in three planes thereby allowing the practitioner to locate the humeral head in the same position as the organic humeral head which is being replaced.

The components of the invention may also provide utility in other prosthetic joints such as prosthetic hip joints.

The interior tapered bore of the humeral head is preferably located offset from the axis of the head. The slot in the intermediate head component is preferably defined by three walls and extends diametrically through the entire component.

The peg of the trunnion component preferably is formed as an integral part of a humeral stem component. Alternatively, the peg of the trunnion component has a square cross section and extends from a square base which is attachable to a humeral stem component.

Additional objects and advantages of the invention will become apparent to those skilled in the art upon reference to the detailed description taken in conjunction with the provided figures.

DETAILED DESCRIPTION OF THE PREFERRED EMBODIMENTS

Referring first to FIGS. 3–9 generally, the modular components of the present invention include a plurality of different sized humeral heads 100, each having a spherical outer surface 102 and an interior tapered bore 104, a frustroconical intermediate head component 200 dimensioned to lockingly mate with the tapered bore of the humeral heads 100 and having a diametrical slot 202, and a humeral stem trunnion component 300 having a rectilinear peg 302 dimensioned to lockingly engage the diametrical slot 202 in the intermediate head component 200.

Figure 3:
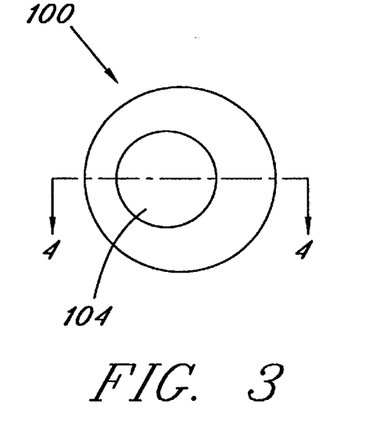
FIG. 3 is a not-to-scale plan view of the bottom of a humeral head component according to the invention.
Figure 4:
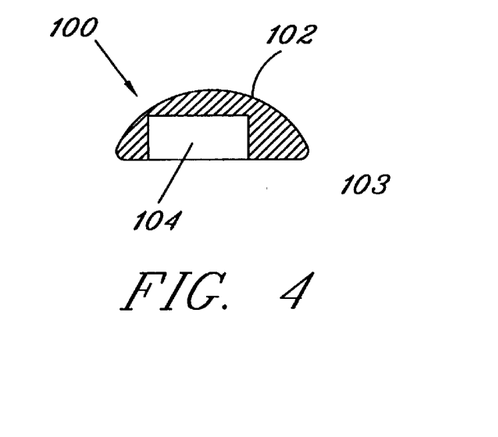
FIG. 4 is a not-to-scale sectional view taken along line 4—4 of FIG. 3.

Referring in particular to FIGS. 3 and 4, an exemplary embodiment of a head 100 has a surface 102 defined by a surface radius of approximately 0.79 inches. The surface is not exactly "hemispherical" since it is less than one half of a sphere having a height of approximately 0.58 inches. The tapered bore 104 is off set from the geometrical center of the surface 102 by approximately 0.118 inches, has a nominal diameter of 0.759 inches plus or minus 0.001 inch, and a taper angle of approximately 2 degrees 51 minutes 28 seconds plus or minus 4 minutes.

The bore 104 has a depth of approximately 0.375 inches. Preferably, the lower edge 103 of the surface 102 is provided with a radius edge of approximately 0.06 inches.

Figure 5:
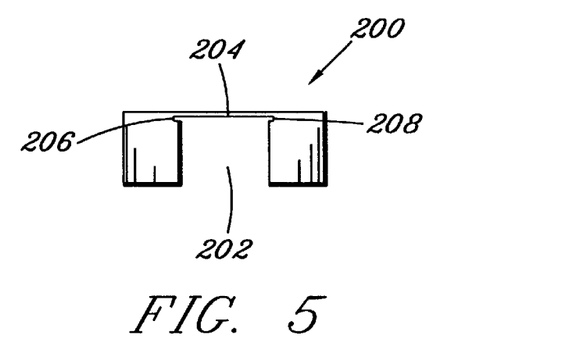
FIG. 5 is a not-to-scale side elevational view of an intermediate had component according to the invention.
Figure 6:
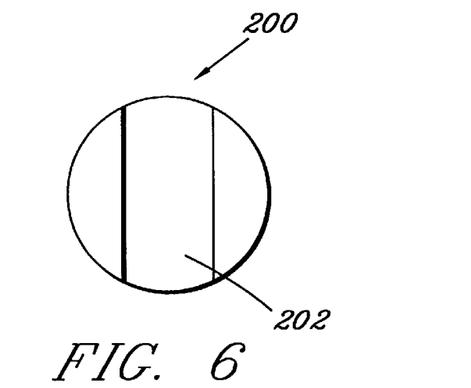
FIG. 6 is a not-to-scale bottom plan view of the component of FIG. 5.

An exemplary embodiment of the intermediate component 200 is shown in FIGS. 5 and 6.

The frustroconical component 200 has a maximum diameter of approximately 0.766882 inches and a minimum diameter of approximately 0.752 inches defining a taper angle of approximately 2 degrees 50 minutes 30 seconds plus or minus 3 minutes.

The diametrical slot 202 is aligned with the diameter of the component 200 and is approximately 0.378 plus or minus 0.001 inches wide. The overall height of the component 200 is approximately 0.300 inches and the slot 202 extends approximately 0.270 inches through the component defining a relatively thin wall top 204 whereby the component may be deformed so as to reduce the width of the slot 202.

In furtherance of this function, the slot is provided with a pair of stress relieving radiused grooves 206, 208 adjacent the top 204. Each groove has a radius of approximately 0.02 inches.

Figure 7:
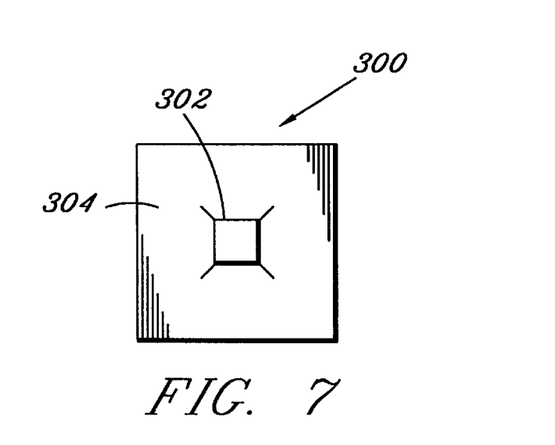
FIG. 7 is a not-to-scale top plan view of the component of FIG. 7.
Figure 8:
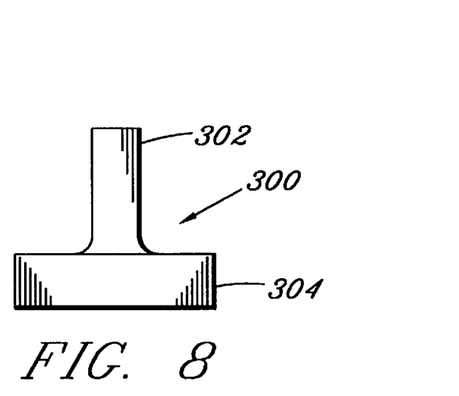
FIG. 8 is a not-to-scale side elevational view of a trunnion component according to the invention.

FIGS. 7 and 8 show an exemplary embodiment of a trunnion component 300 according to the invention.

The peg 302 of the trunnion component 300 is approximately 1.00 inch tall and has an approximately 0.375 plus or minus 0.001 inch square cross section.

As shown in FIGS. 7 and 8, the peg 302 extends orthogonally from an approximately 0.5 inch thick and approximately 1.50 inch square base 304. According to this embodiment of the invention a humeral stem component having a recess for receiving the base 304 will be provided and the base will be affixed to the stem component.

Figure 9:
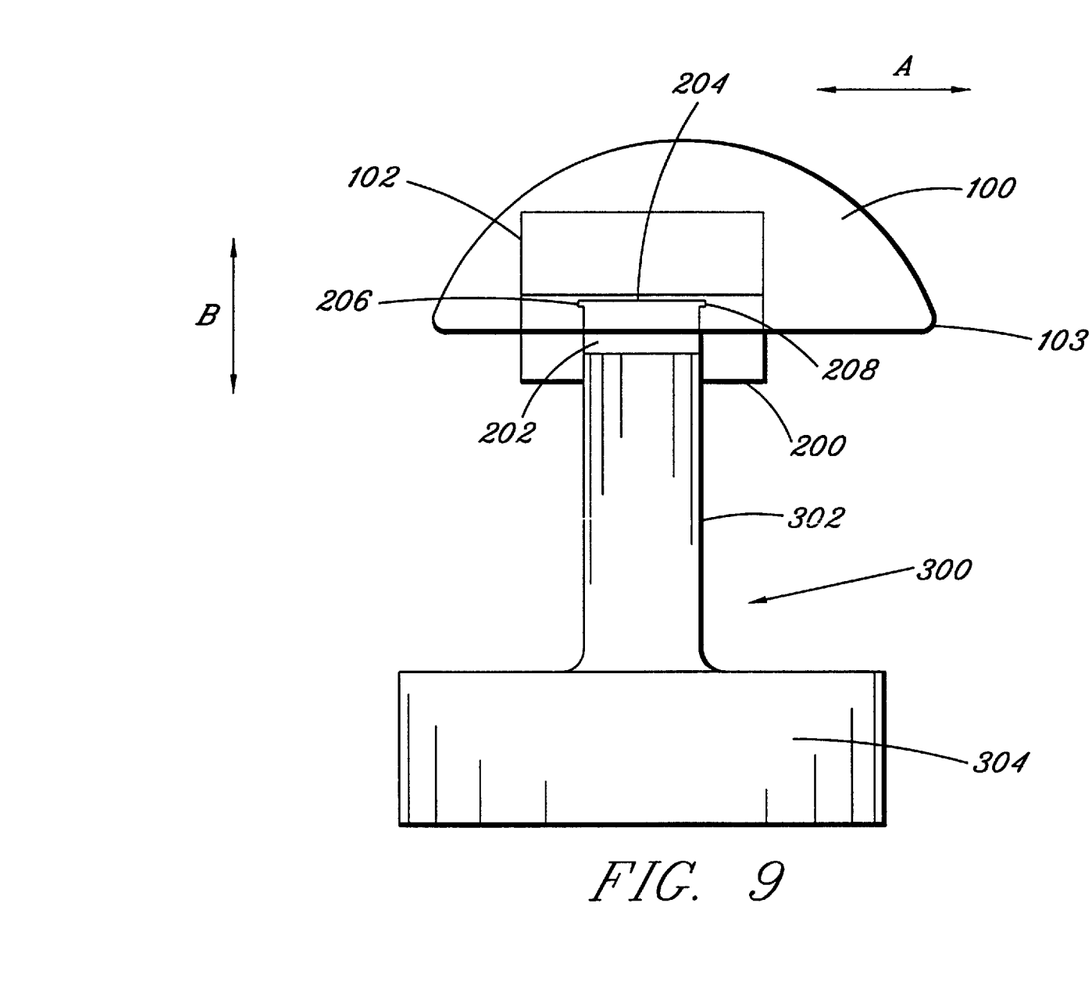
FIG. 9 is a transparent side elevational view of the components of the invention partially assembled.
Figure 10:
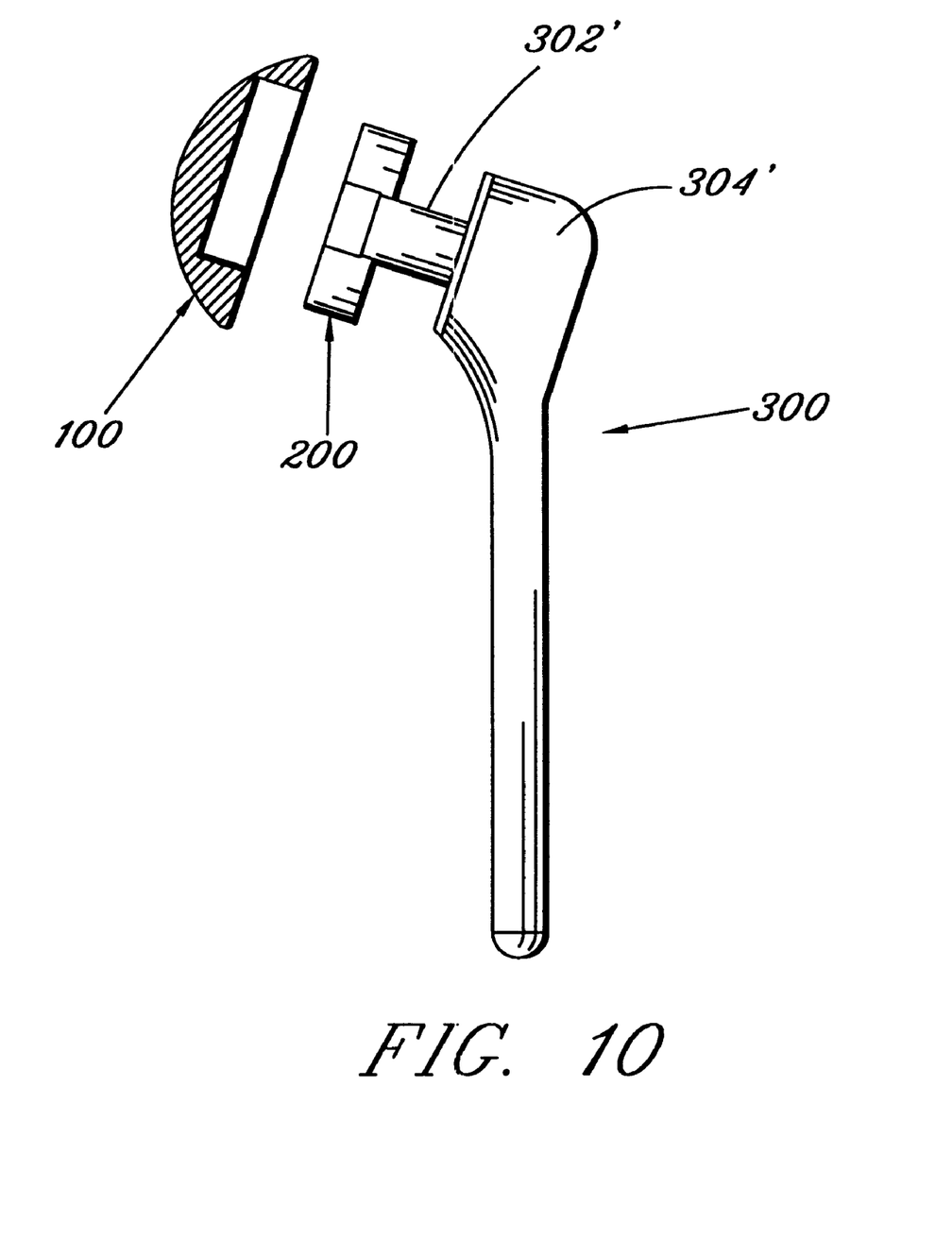
FIG. 10 illustrates a presently preferred embodiment of the invention with the trunnion component being formed as a humeral stem with an integral peg.

Alternatively, according to a preferred embodiment of the invention as shown in FIG. 10 (to be described hereinafter), the peg is made an integral part of the stem component Turning first to FIG. 9, from the foregoing, those skilled in the art will appreciate that the components are assembled by partially inserting the intermediate head component 200 into the tapered bore 102 of a humeral head 100 without forcing the components together. The peg 302 of the trunnion component 300 is then located in the slot 202 of the intermediate head component 200.

In this partially assembled state which is shown in FIG. 9, the head 100 is movable relative to the trunnion component 300 in at least four directions, actually in an infinite number of directions.

For example, the head 100 may be rotated about the intermediate component 200 in the direction illustrated by arrows "A"; the head 100 and intermediate component 200 together may be tilted relative to the trunnion component 300 in the direction illustrated by the arrows "B"; the head 100 and intermediate component 200 together may be translated relative to the trunnion component 300 in a direction perpendicular to the page (i.e., back and forth); and the head 100 and the intermediate component 200 can be moved up and down relative to the trunnion component 300. This allows the practitioner a substantial range of adjustment, i.e., at least four degrees of freedom.

Once the head 100 is located in the correct orientation, the components are pressed together. The intermediate head component 200 taper locks with the humeral head 100 and force-fit locks onto the peg 302 of the trunnion component 300.

Finally, as mentioned above, FIG. 10 illustrates a presently preferred embodiment of the invention wherein the trunnion component 300' is formed as a humeral stem component 304' with an integral peg 302' which is located and dimensioned to couple with components 100 ans 200. Those skilled in the art will readily appreciate that the intermediate component 200 may be rotated from the position shown in FIG. 10 thereby allowing sliding and tilting of intermediate component 200 relative to peg 302'.

There have been described and illustrated herein modular prosthetic shoulder components. While particular embodiments of the invention have been described, it is not intended that the invention be limited thereto, as it is intended that the invention be as broad in scope as the art will allow and that the specification be read likewise. For example, as described above, the components of the invention may also be advantageously used in other prosthetic joints such as prosthetic hip joints.

It will therefore be appreciated by those skilled in the art that yet other modifications could be made to the provided invention without deviating from its spirit and scope as so claimed.

What is claimed is:

1. A modular prosthetic joint component, comprising:
   (a) a head component having a convex surface and a tapered internal bore;
   (b) an intermediate component having a body with an outer surface dimensioned to lockingly engage said internal bore, said body of said intermediate component having a slot; and
   (c) a trunnion component dimensioned to be lockingly engaged by said slot, wherein said internal bore and said slot permit said head component to be oriented relative to said trunnion component in at least two different planes before locking engagement.

2. A modular prosthetic joint component according to claim 1, wherein said internal bore and slot permit said head component to be oriented relative to said trunnion component in at least three different planes before locking engagement.

3. A modular prosthetic joint component according to claim 1, wherein at least a part of said outer surface said intermediate component is frustroconical.

4. A modular prosthetic joint component according to claim 3, wherein said slot is a diametrical slot formed internally of said frustroconical outer surface.

5. A modular prosthetic joint component according to claim 4, wherein said frustroconical outer surface of said intermediate component is dimensioned to deform when inserted into said tapered bore.

6. A modular prosthetic joint component according to claim 5, wherein said trunnion component includes a peg dimensioned to fit into said diametrical slot and oriented before locking said turnnion to said intermediate component when said slot is deformed.

7. A modular prosthetic shoulder joint component, comprising:
   (a) a humeral head component having a convex surface and a tapered internal bore;
   (b) an intermediate head component having an outer surface dimensioned to lockingly engage said bore, said intermediate head component having a slot; and
   (c) a trunnion component dimensioned to be lockingly engaged by said slot, wherein said internal bore and slot permit said humeral head component to be oriented relative to said trunnion component in at least two different planes before locking engagement.

8. A modular prosthetic shoulder joint component according to claim 7, wherein said internal bore and slot permit said head component to be oriented relative to said trunnion component in at least three different planes before locking engagement.

9. A modular prosthetic shoulder joint component according to claim 7, wherein said tapered bore is offset from the geometrical center of said humeral head component.

10. A modular prosthetic shoulder joint component according to claim 9, wherein said convex surface has a substantially constant radius.

11. A modular prosthetic shoulder joint component according to claim 7, wherein said intermediate head component has at least a part of an outer surface which is substantially frustroconical.

12. A modular prosthetic shoulder joint component according to claim 11, wherein said slot is a diametrical slot formed intermediate said outer surface.

13. A modular prosthetic shoulder joint component according to claim 12, wherein said slot of said intermediate head component is dimensioned to deform when inserted into said tapered bore.

14. A modular prosthetic shoulder joint component according to claim 13, wherein said trunnion component includes a peg dimensioned to fit into said diametrical slot and oriented before locking said trunnion to said intermediate component when said slot is deformed.

15. A method of attaching a first prosthetic joint component to a second prosthetic joint component, comprising the steps of:
   (a) providing the first component with an internal tapered bore;
   (b) providing an intermediate component dimensioned to lockingly engage the bore;
   (c) providing the intermediate component with a slot;
   (d) dimensioning a second component to be lockingly engaged by said slot;
   (e) partially inserting the intermediate component in the bore and partially inserting the second component in the slot; and
   (f) orienting the first component relative to the second component in at least two different planes before locking engagement.

16. A method according to claim 15, further comprising the step of pressing the first component, intermediate component, and second component together to locking engagement.

17. A method according to claim 15, wherein the intermediate component has an outer surface at least part of which is frustroconical.

18. A method according to claim 17, wherein said slot is a diametrical slot formed intermediate said frustroconical outer surface.

19. A method according to claim 18, wherein said slot of said the frustroconical intermediate component is dimensioned to deform when inserted into the tapered bore.

20. A modular prosthetic joint component, comprising:
   (a) a head component having a convex surface and a tapered internal bore;
   (b) an intermediate component having a body with an outer surface dimensioned to lockingly engage said bore, said intermediate component further comprising a slot that includes two parallel walls; and
   (c) a trunnion component further comprising a peg component that includes a pair of parallel surfaces dimensioned to be lockingly engaged by said parallel walls, wherein said head component may be oriented relative to said trunnion component in at least two different planes before said intermediate component lockingly engages said bore and said peg is lockingly engaged by said parallel walls.

21. A modular prosthetic joint component, comprising:
   (a) a head component having a convex surface and a internal bore;
   (b) an intermediate component having an outer surface dimensioned to lockingly engage said bore, said intermediate component further comprising a slot that includes two parallel walls; and
   (c) a trunnion component further comprising a peg component that includes a pair of parallel surfaces dimensioned to be lockingly engaged by said parallel walls, wherein said intermediate component may be translated and tilted relative to said peg before the parallel walls of said intermediate component lockingly engages the parallel surfaces of said peg.

22. A modular prosthetic joint comprising:
   a connector having a top surface, a bottom surface, a generally conical outer surface extending between said top and bottom surfaces and a diametrical slot internal of said outer surfaces forming a pair of segments, said slot open at diametric ends thereof and at said bottom surface;
   a stem having a trunnion extending from an end thereof for engagement with said internal slot, said trunnion having at least two sidewalls for engaging an internal wall of each side segment; and
   a head having a bearing surface and a tapered internal bore for receiving said conical outer surfaces of said connector wherein said head component is capable of being oriented relative to said trunnion component in at least two different planes before locking engagement.

23. The modular prosthetic joint as set forth in claim 22, wherein said bearing surface has a generally spherical shape and said tapered bore is offset with respect to a central axis of said bearing surface.

24. The modular prosthetic joint as set forth in claim 22, wherein a relief groove is formed in each wall of said side segments of said slot along a line of contact between said walls and a roof of said slot opposite said bottom surface.

25. The modular prosthetic joint as set forth in claim 24, wherein said slot walls are deflected inwardly about said relief grooves upon insertion of said connector into said tapered bore in said head.

26. The modular prosthetic joint as set forth in claim 22, wherein said tapered bore in said head is a frustroconically tapered bore.

* * * * *

UNITED STATES PATENT AND TRADEMARK OFFICE
CERTIFICATE OF CORRECTION

PATENT NO. : 6,129,764
DATED : October 10, 2000
INVENTOR(S) : Servidio

It is certified that error appears in the above-identified patent and that said Letters Patent is hereby corrected as shown below:

Column 1, line 45, "On" should read -- One --.
Column 1, line 49, "an" should read -- a --.
Column 3, line 47, "had" should read -- head --.
Column 3, line 50, before "component" insert -- trunnion --; cancel the word "of" (second occurrence).
Column 3, line 51, cancel the words "FIG. 7".
Column 4, line 12, "off set" should read -- offset --.
Column 5, line 20, "ans" should read -- and --.
Column 5, line 57, after "surface" insert -- of --.
Column 7, line 2, cancel the word "the".
Column 7, line 21, "a" (third occurrence) should read -- an --.
Column 7, line 23, after "having" insert -- a body with --.
Column 7, line 33, "engages" should read -- engage --.

Signed and Sealed this

Twenty-fourth Day of April, 2001

*Attest:*

NICHOLAS P. GODICI

*Attesting Officer*   Acting Director of the United States Patent and Trademark Office